US010517367B2

(12) United States Patent
Bureiko et al.

(10) Patent No.: US 10,517,367 B2
(45) Date of Patent: Dec. 31, 2019

(54) METHOD OF TREATING HAIR WITH FOAM

(71) Applicant: Noxell Corporation, Hunt Valley, MD (US)

(72) Inventors: Andrei Sergeevich Bureiko, Cincinnai, OH (US); George Scott Kerr, Mason, OH (US); Jennifer Louise Searles, Mason, OH (US); Brandon Scott Lane, Hamilton, OH (US)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 14/175,887

(22) Filed: Feb. 7, 2014

(65) Prior Publication Data

US 2014/0216495 A1 Aug. 7, 2014

Related U.S. Application Data

(60) Provisional application No. 61/762,120, filed on Feb. 7, 2013, provisional application No. 61/815,424, filed on Apr. 24, 2013.

(51) Int. Cl.
*A61K 8/18* (2006.01)
*A45D 19/02* (2006.01)
(Continued)

(52) U.S. Cl.
CPC ............ *A45D 19/02* (2013.01); *A45D 19/00* (2013.01); *A45D 2019/0066* (2013.01); *A45D 2200/25* (2013.01); *B05B 11/0089* (2013.01)

(58) Field of Classification Search
CPC ........ B65D 83/00; B65D 83/14; B65D 83/28; B65D 83/303; B65D 83/306;
(Continued)

(56) References Cited

U.S. PATENT DOCUMENTS 3,414,171 A * 12/1968 Grisham et al. ......... 222/402.14
4,273,144 A * 6/1981 Morganroth ............. A45D 7/04 132/270

(Continued)

FOREIGN PATENT DOCUMENTS

CN 101522069 A 9/2009
CN 101668508 A 3/2010

(Continued)

OTHER PUBLICATIONS

"Japanese Application Serial No. 2015-556198, Response filed Oct. 23, 2017 to Office Action dated Apr. 25, 2017", (w/ Translation of Amended Claims). 11 pgs.

(Continued)

*Primary Examiner* — Rachel R Steitz
(74) *Attorney, Agent, or Firm* — Schwegman Lundberg & Woessner, P.A.

(57) ABSTRACT

A method of treating hair more precisely including providing a hair treatment composition in a foam dispenser, dispensing the hair treatment composition directly onto the hair as a foam, leaving the foam on the hair, and rinsing the foam from the hair. The foam dispenser includes a reservoir for holding the hair treatment composition, an extended nozzle connected to the reservoir, and one or more nozzle orifices. The one or more nozzle orifices has a total orifice area of from about 5 $mm^2$ to about 80 $mm^2$. The extended nozzle has a protrusion length of from about 20 mm to about 125 mm. The foam has a specific volume of from about 4 ml/g to about 20 ml/g.

11 Claims, 4 Drawing Sheets

(51) Int. Cl.
*A45D 19/00* (2006.01)
*B05B 11/00* (2006.01)

(58) Field of Classification Search
CPC .... B65D 83/384; B65D 83/386; A61K 8/046; A61K 8/89; A61K 2800/87; A61K 2800/58; A61Q 5/00
USPC .............. 222/402.1, 402.12, 402.13, 402.14; 132/112–116, 208; 424/47; 8/405
See application file for complete search history.

(56) References Cited

U.S. PATENT DOCUMENTS

| | | | | |
|---|---|---|---|---|
| 4,815,637 | A * | 3/1989 | Nellis | 222/402.12 |
| 5,307,964 | A * | 5/1994 | Toth | 222/402.13 |
| 7,040,507 | B2 * | 5/2006 | Koike et al. | 222/94 |
| 2001/0042553 | A1 | 11/2001 | Duqueroie | |
| 2002/0017575 | A1 * | 2/2002 | Andrews | B05B 1/14 239/337 |
| 2002/0177534 | A1 * | 11/2002 | Paul | A61Q 9/02 510/130 |
| 2006/0081659 | A1 * | 4/2006 | Walker | 222/402.1 |
| 2007/0184011 | A1 * | 8/2007 | Herlands | 424/73 |
| 2010/0126522 | A1 | 5/2010 | Fujinuma et al. | |
| 2010/0126523 | A1 * | 5/2010 | Fujinuma et al. | 132/221 |
| 2011/0284586 | A1 * | 11/2011 | Kerr et al. | 222/190 |
| 2012/0152270 | A1 * | 6/2012 | Hazan | A61K 8/046 132/208 |
| 2013/0206159 | A1 | 8/2013 | Kodama | |
| 2014/0060568 | A1 | 3/2014 | Lane et al. | |

FOREIGN PATENT DOCUMENTS

| | | | |
|---|---|---|---|
| CN | 102665820 | A | 9/2012 |
| CN | 104955357 | A | 9/2015 |
| JP | 6439288 | U | 3/1989 |
| JP | 10235238 | A | 9/1998 |
| JP | 2001309814 | A | 11/2001 |
| JP | 2008291024 | A | 12/2008 |
| JP | 2012071114 | A | 4/2012 |
| JP | 2013514996 | A | 5/2013 |
| JP | 2016515839 | A | 6/2016 |
| WO | WO-2011075657 | A2 | 6/2011 |
| WO | WO2013019858 | A1 | 2/2013 |
| WO | WO-2014123798 | A1 | 8/2014 |

OTHER PUBLICATIONS

"Chinese Application Serial No. 201480006330.X, Office Action dated Jan. 23, 2017", (w/ English Translation), 17 pgs.
"Chinese Application Serial No. 20140006330.X, Office Action dated Aug. 25, 2017", (w/ English Translation), 15 pgs.
"Chinese Application Serial No. 201480006330.X, Response filed Jun. 5, 2017 to Office Action dated Jan. 23, 2017", (w/ English Translation of Claims), 12 pgs.
"Japanese Application Serial No. 2015-556198, Office Action dated Apr. 25, 2017", (w/ English Translation), 8 pgs.
"Canadian Application Serial No. 2,899,227 Office Action dated Jan. 10, 2017", 3 pgs.
"Canadian Application Serial No. 2,899,227, Office Action dated Apr. 11, 2016", 3 pgs.
"Canadian Application Serial No. 2,899,227, Response filed Jun. 23, 2016 to Office Action dated Apr. 11, 2016", 10 pgs.
"European Application Serial No. 14704742.7, Office Action dated Sep. 15, 2015", 2 pgs.
"European Application Serial No. 14704742.7, Office Action dated Nov. 3, 2016", 5 pgs.
"European Application Serial No. 14704742.7, Reply filed Mar. 23, 2016 to Office Action dated Sep. 15, 2015", 4 pgs.
"European Application Serial No. 14704742.7, Response filed Feb. 8, 2017 to Office Action dated Nov. 3, 2016", 4 pgs.
"International Application Serial No. PCT/US2014/014382, International Preliminary Report on Patentability dated Aug. 20, 2015", 7 pgs.
"International Application Serial No. PCT/US2014/014382, International Search Report dated May 15, 2014", 3 pgs.
"International Application Serial No. PCT/US2014/014382, Written Opinion dated May 15, 2015", 5 pgs.
"Japenese Application Serial No. 2015-556198, Office Action dated Oct. 4, 2016", (w/ English Translation), 11 pgs.
"Japanese Application Serial No. 2015-556198, Response filed Dec. 19, 2016 to Office Action dated Oct. 4, 2016", W/ English Translation of Claims, 15 pgs.
"Japanese Application Serial No. 2015-556198, Examiners Decision of Final Refusal dated Jul. 31, 2018", W/ English Translation, 15 pgs.
"Japanese Application Serial No. 2015-556198, Response filed Nov. 29, 2018 to Examiners Decision of Final Refusal dated Jul. 31, 2018", w/ English Claims, 42 pgs.
"Japanese Application Serial No. 2015-556198, Pre-Trial Examination Report dated Feb. 1, 2019", w/ English Translation, 7 pgs.
"Japanese Application Serial No. 2015-556198, Response filed Apr. 26, 2019 to Pre-Trial Examination Report dated Feb. 1, 2019", w/ English Claims, 8 pgs.
"Japanese Application Serial No. 2015-556198, Notification of Reasons for Refusal dated Oct. 21, 2019", W/ English Translation, 5 pgs.

* cited by examiner

METHOD OF TREATING HAIR WITH FOAM

FIELD OF THE INVENTION

The present invention relates to a method of treating hair more precisely. More particularly, the present invention relates to a method of treating hair more precisely comprising providing a hair treatment composition in a foam dispenser having an extended nozzle and dispensing the hair treatment composition directly onto the hair as a foam.

BACKGROUND OF THE INVENTION

Various methods are known for coloring and bleaching the hair. These methods include the application of liquid hair treatment compositions and foam hair treatment compositions. Known methods including each of these compositions have drawbacks.

Known liquid hair treatment methods can be messy—liquid often runs down the skin of the scalp onto the face and the neck. To address the drawbacks of liquid hair treatment methods, foam hair treatment methods have been developed. Unlike liquids, foam does not run down the skin of the scalp onto the face and the neck.

However, the current structure of foam dispensers makes dispensing foam directly onto the hair difficult to achieve without losing precision and control. Therefore, current foam hair treatment methods direct consumers to first dispense the foam into the hand rather than directly onto the hair. Dispensing foam into the hand results in a lack of precision and control in the application of the foam to the hair, especially to the roots.

Based on the foregoing, there is a need for a method of treating the hair more precisely which includes a foam dispenser designed for dispensing foam directly onto the hair.

SUMMARY OF THE INVENTION

According to an embodiment of the invention, there is provided a method of treating hair more precisely, the method comprising (a) providing a hair treatment composition in a foam dispenser, wherein the foam dispenser comprises (i) a reservoir for holding the hair treatment composition; (2) an extended nozzle fluidly connected to the reservoir; wherein the extended nozzle comprises one or more nozzle orifices; wherein the one or more nozzle orifices has a total orifice area of from about 5 $mm^2$ to about 80 $mm^2$; and wherein the extended nozzle has a protrusion length of from about 20 mm to about 125 mm; (b) dispensing the hair treatment composition from the reservoir into the extended nozzle and out the one or more nozzle orifices directly onto the hair as a foam; wherein the foam has a specific volume of from about 4 ml/g to about 20 ml/g; (c) leaving the foam on the hair for from about 5 minutes to about 60 minutes; and (d) rinsing the foam from the hair.

According to yet another embodiment of the invention, there is provided a hair treatment kit comprising (a) a hair treatment composition selected from the group consisting of hair colorant compositions, hair bleaching compositions, highlighting compositions, conditioning compositions, and combinations thereof; (b) a foam dispenser comprising (i) a reservoir for holding the hair treatment composition; (ii) an extended nozzle fluidly connected to the reservoir; wherein the extended nozzle comprises one or more nozzle orifices; wherein the one or more nozzle orifices have a total orifice area of from about 5 $mm^2$ to about 80 $mm^2$; and wherein the extended nozzle has a protrusion length from about 20 mm to about 125 mm; and (c) a set of instructions comprising directing a user to dispense the hair treatment composition directly from the foam dispenser onto the hair as a foam.

These and other features, aspects, and advantages of the present invention will become evident to those skilled in the art from a reading of the present disclosure.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

DETAILED DESCRIPTION OF THE INVENTION

Figure 2:
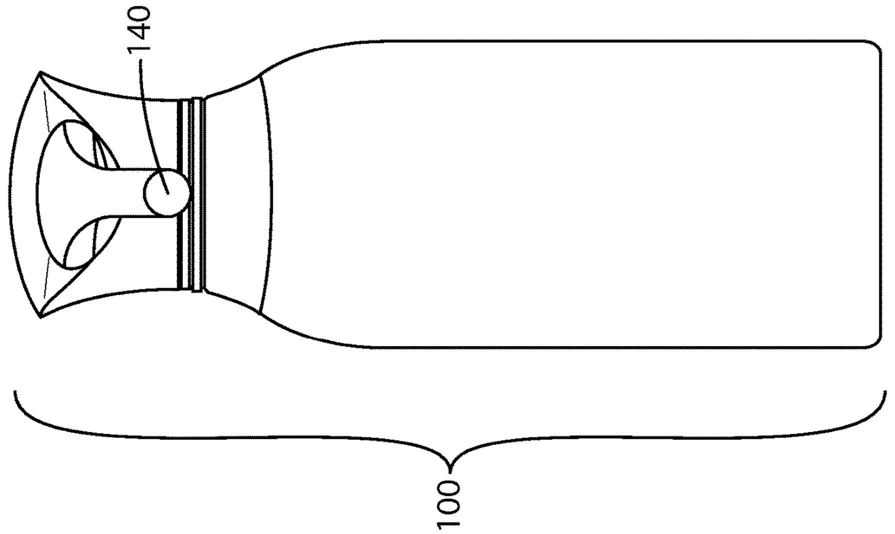
FIG. 2 is a right side view of the foam dispenser of FIG. 1.

In all embodiments described below, all percentages are by weight of the total composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated. The term “weight percent” may be denoted as “wt. %” herein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The method of treating hair more precisely may comprise (a) providing a hair treatment composition in a foam dispenser; (b) dispensing the hair treatment composition directly onto the hair as a foam; (c) leaving the foam on the hair for from about 5 minutes to about 60 minutes; and (d) rinsing the foam from the hair.

The foam dispenser may comprise a reservoir for holding the hair treatment composition and an extended nozzle fluidly connected to the reservoir.

A. Foam Dispenser

Figure 1:
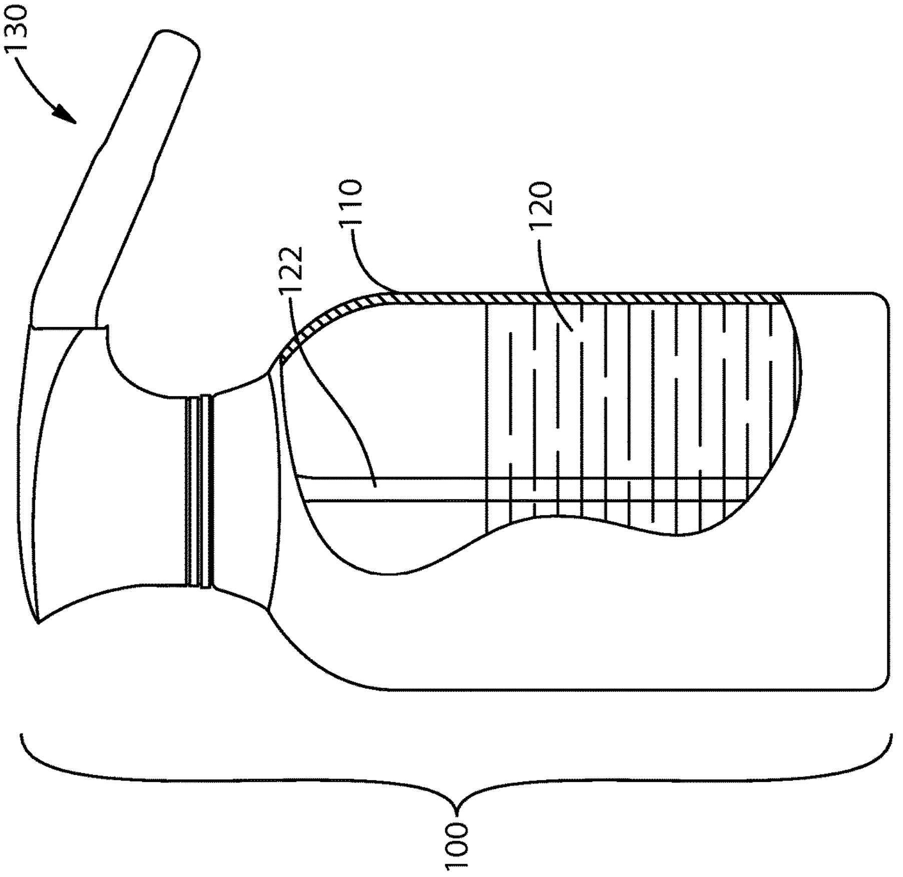
FIG. 1 is a front view of an embodiment of the foam dispenser.

Referring to FIG. 1, the method of treating hair more precisely may comprise providing a hair treatment composition 120 in a foam dispenser 100. The foam dispenser 100 may be selected from the group consisting of squeeze foam dispensers, aerosol foam dispensers, pump foam dispensers, other mechanical foam dispensers, and combinations thereof. In an embodiment, the foam dispenser 100 may be a dual aerosol foam dispenser 100, and the hair treatment composition 120 may be mixed while being dispensed as a foam.

1) Reservoir

Referring to FIG. 1, the foam dispenser 100 may comprise a reservoir 110 for holding a hair treatment composition 120. The reservoir 110 may be made out of any suitable material selected from the group consisting of plastic, metal, alloy, laminate, and combinations thereof. The reservoir 110 may be a refillable reservoir 110 such as a pour-in or screw-on reservoir 110, or the reservoir 110 may be for one-time use. The reservoir 110 may also be removable from the foam dispenser 100. Alternatively, the reservoir 110 may be integrated with the foam dispenser 100. In an embodiment, there may be two or more reservoirs 110.

In an embodiment, the reservoir 110 may be comprised of a material selected from the group consisting of rigid materials, flexible materials, and combinations thereof. The reservoir 110 may be comprised of a rigid material if it does not collapse under external atmospheric pressure when it is subject to an interior partial vacuum. In an embodiment, the reservoir 110 may be pressurized.

In an embodiment, the reservoir 110 may hold a hair treatment composition 120. The hair treatment composition 120 may be a liquid and may have a viscosity of from about 1 cps to about 2,000 cps, alternatively from about 100 cps to about 1,000 cps, and alternatively from about 300 cps to about 600 cps.

The viscosity of the hair treatment composition 120 may be measured at 25° C. by a TA Instruments AR2000 rheometer or similar equipment. A 40 mm 2° stainless steel cone geometry may be used for the viscosity measurements. The viscosity may be recorded at a constant shear rate of 6.6 $s^{-1}$ after 1 minute. The viscosity measurement may be run 3 times and the average of the 3 times may be calculated. If the hair treatment composition 120 is supplied as two or more individual components which require mixing prior to application, the viscosity measurement may start immediately after mixing the components.

The hair treatment composition 120 may include components selected from the group consisting of solvents, oxidative dyes, direct dyes, oxidizing agents, radical scavengers, rheology modifiers, chelants, pH modifiers, buffering agents, carbonate ion sources, peroxymonocarbonate ion sources, surfactants, polymers, fragrances, enzymes, dispersing agents, peroxide stabilizing agents, antioxidants, plant extracts, conditioning agents, ceramides, preserving agents, opacifiers, pearling agents, and mixtures thereof.

In an embodiment, the hair treatment composition 120 may be a hair color composition or a hair bleaching composition. The hair treatment composition 120 may be supplied as two or more individual components which may require mixing prior to application. The hair color composition 120 may comprise an oxidative dyeing composition and/or a direct dyeing composition. The oxidative dying composition may comprise an oxidizing agent.

2) Extended Nozzle

Still referring to FIG. 1, the foam dispenser 100 may comprise an extended nozzle 130. The extended nozzle 130 may be fluidly connected to the reservoir 110 and may include any part of the foam dispenser 100 that may protrude beyond the outermost contour of the reservoir 110. In an embodiment, the extended nozzle 130 may be fluidly connected to the reservoir 110 by a dip tube 122.

The extended nozzle 130 may be composed of any suitable material selected from the group consisting of plastic, metal, alloy, fibrous materials, and combinations thereof. In an embodiment the extended nozzle 130 may be composed of a polymer selected from the group consisting of polyethylene, polypropylene, polyethylene terephthalate, polycarbonate, polystyrene, ethyl vinyl alcohol, polyvinyl alcohol, polyvinyl chloride, thermoplastic elastomer, and combinations thereof.

The extended nozzle 130 may be made by a process selected from the group consisting of blow molding, compaction plus sintering, compression molding, expandable bead molding, extrusion molding, foam molding, injection molding, laminating, reaction injection molding, matched molding, matrix molding, plastic molding, pressure plug assist molding, rotational molding, transfer molding, thermoforming, vacuum forming, and combinations thereof.

In an embodiment, the extended nozzle 130 may be removable from the foam dispenser 100 and may comprise one or more components. Alternatively, the extended nozzle 130 may be integrated with the foam dispenser 100. The extended nozzle 130 may be selected from the group consisting of detachable nozzles, telescoping nozzles, flexible nozzles, hinged nozzles, and combinations thereof.

Referring to FIG. 2, the extended nozzle 130 may comprise one or more nozzle orifices 140 located distally from the reservoir 110 of the foam dispenser 100. The one or more nozzle orifices 140 may have a total orifice area of from about 3 $mm^2$ to about 133 $mm^2$, alternatively from about 5 $mm^2$ to about 80 $mm^2$, alternatively from about 12 $mm^2$ to about 60 $mm^2$, and alternatively from about 20 $mm^2$ to about 50 $mm^2$. In an embodiment with more than one nozzle orifice 140, the total orifice area is the summation of the individual nozzle orifice areas.

Figure 3:
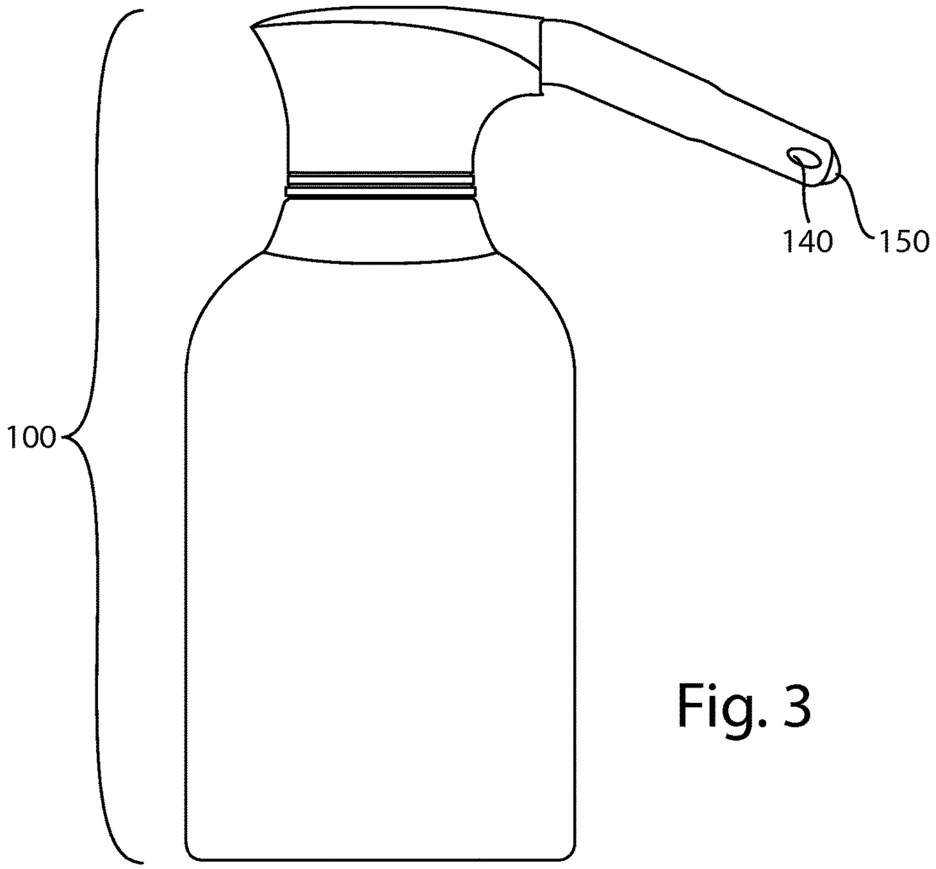
FIG. 3 is a front view of an embodiment of the foam dispenser.

Referring to FIG. 3, the extended nozzle 130 may comprise a closed nozzle tip 150, and the one or more nozzle orifices 140 may be offset from the closed nozzle tip 150.

The closed nozzle tip 150 may be removable from the extended nozzle 130 or may be integrated with the extended nozzle 130.

Figure 4:
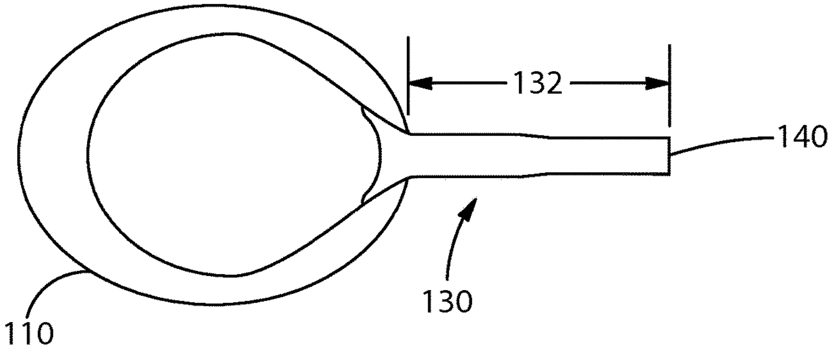
FIG. 4 is a top view of the foam dispenser of FIG. 1.
Figure 5:
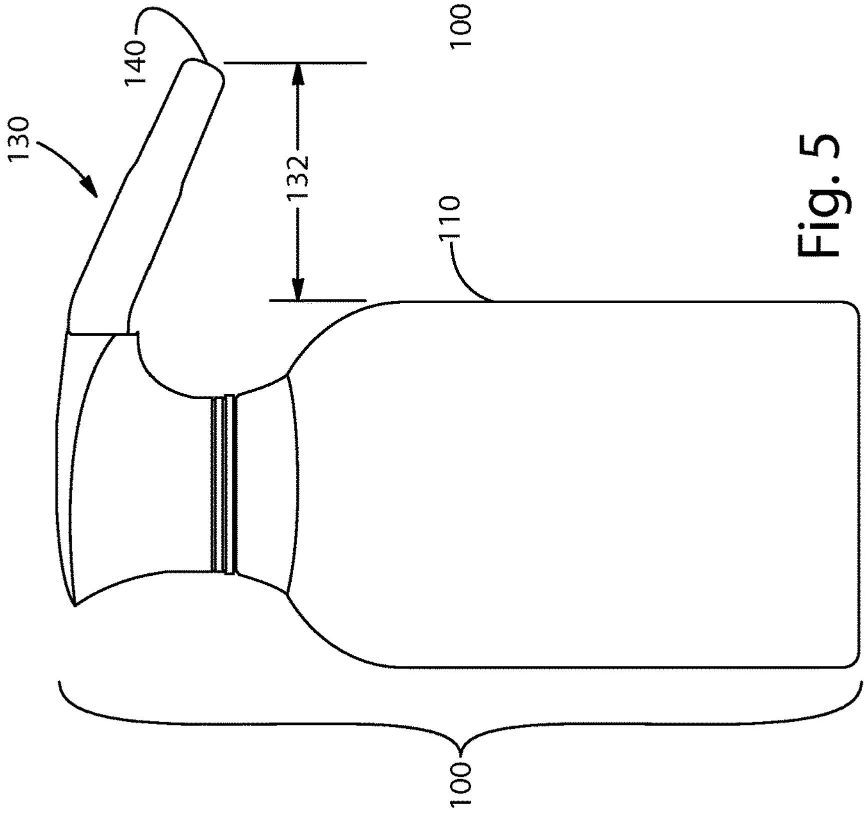
FIG. 5 is a front view of the foam dispenser of FIG. 1.

Referring to FIGS. 4 and 5, the extended nozzle 130 may have a protrusion length 132. The protrusion length 132 may be the distance that the one or more nozzle orifices 140 protrudes from the outer contour of the reservoir 110. The protrusion length 132 may be from about 20 mm to about 125 mm, alternatively from about 35 mm to about 110 mm, alternatively from about 40 mm to about 75 mm, and alternatively from about 45 mm to about 70 mm.

Figure 6:
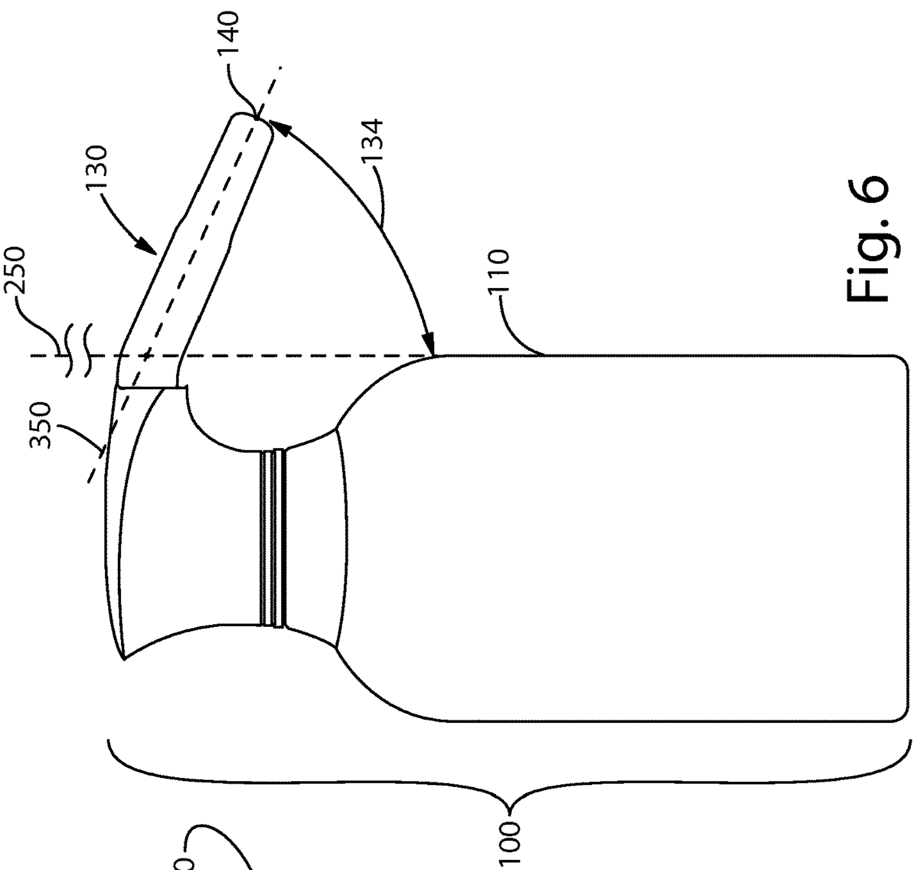
FIG. 6 is a front view of the foam dispenser of FIG. 1.

Referring to FIG. 6, the extended nozzle 130 may have a nozzle angle 134. To measure the nozzle angle 134, the foam dispenser 100 may have vertical axis 250 which extends from the outer contour of the reservoir 110 and intersects with the extended nozzle 130. The foam dispenser 100 may also have a nozzle axis 350 which extends from (1) where the vertical axis 250 intersects the center of the extended nozzle 130 to (2) the center of the one or more nozzle orifices 140. The nozzle angle 134 may be the angle formed by the vertical axis 250 and the nozzle axis 350. The nozzle angle 134 may be greater than 70° and less than 120°, alternatively from about 75° to about 115°, alternatively greater than 70° and less than 100°, and alternatively from about 75° to about 95°.

B. Method of Treating Hair

The method of treating hair more precisely may comprise providing a hair treatment composition 120 in a foam dispenser 100 as described above.

The method of treating hair more precisely may further comprise dispensing the hair treatment composition 120 from the reservoir 110 into the extended nozzle 130 and out the one or more nozzle orifices 140 directly onto the hair as a foam.

The foam may have a specific volume of from about 4 ml/g to about 20 ml/g, alternatively from about 5 ml/g to about 15 ml/g, and alternatively from about 6 ml/g to about 10 ml/g. In an embodiment, the foam specific volume may be measured by placing a 100 ml beaker onto a mass balance, tarring the mass of the beaker and then dispensing from a foam dispenser into the 100 ml beaker until the volume of the foam is equal to 100 ml. Record the resulting mass of the 100 ml of foam at 5 seconds from the end of dispensing. Dividing the volume (100) by the mass of the foam results in the foam specific volume having the units of ml/g. The experiment may be repeated 3 times and the average foam specific volume may be calculated.

The foam may be dispensed directly onto the hair as a noodle of foam. In an embodiment, the foam may be dispensed directly onto the hair as multiple noodles of foam. At any time, the noodle of foam may have an average diameter of from about 2 mm to about 50 mm, alternatively from about 5 mm to about 40 mm, and alternatively from about 10 mm to about 30 mm. The noodle of foam may be of any shape selected from the group consisting of flat noodles, cylindrical noodles, square noodles, non-symmetrical noodles, symmetrical noodles, linear noodles, non-linear noodles, and combinations thereof.

The method of treating hair more precisely may further comprise leaving the foam on the hair for from about 5 minutes to about 60 minutes.

The method of treating hair more precisely may further comprise rinsing the foam from the hair.

The method of treating hair more precisely may further comprise using the extended nozzle 130 to part the hair.

C. Hair Treatment Kit

The hair treatment kit may comprise a foam dispenser as described above. The hair treatment kit may also comprise a hair treatment composition selected from the group consisting of hair colorant compositions, hair bleaching compositions, highlighting compositions, conditioning compositions, and combinations thereof. The hair treatment composition may be individually packaged separate from the foam dispenser. In an embodiment, the hair treatment kit may comprise two or more hair treatment compositions which require mixing prior to application.

The hair treatment kit may comprise a set of instructions comprising directing a user to dispense the hair treatment composition directly from the foam dispenser onto the hair as a foam. In an embodiment, the set of instructions may comprise directing a user to dispense the hair treatment composition directly from the foam dispenser onto the hair as a noodle of foam as described above.

EXPERIMENTAL DATA

Referring to Table 1, 17 hair color consumers were asked to simulate using the following extended nozzle foam dispensers with different protrusion lengths. The consumers were then asked to rank the protrusion lengths based on precision and control for dispensing foam directly onto the hair. A ranking of 1 correlates to the most preferred protrusion length, and a ranking of 5 correlates to the least preferred protrusion length. The percentages in Table 1 show how the consumers ranked each protrusion length, rounded to the nearest tenth. The last column of Table 1 shows the percentage of consumers who ranked each protrusion length as most preferred or as second most preferred for precision and control.

TABLE 1

| Protrusion Length | 1 | 2 | 3 | 4 | 5 | 1 + 2 |
|---|---|---|---|---|---|---|
| 5 mm | 5.9% | 5.9% | 11.8% | 5.9% | 70.6% | 11.8% |
| 35 mm | 17.6% | 11.8% | 35.3% | 35.3% | 0% | 29.4% |
| 50 mm | 41.2% | 17.6% | 29.4% | 5.9% | 5.9% | 58.8% |
| 65 mm | 11.8% | 52.9% | 11.8% | 23.5% | 0% | 64.7% |
| 110 mm | 23.5% | 11.8% | 11.8% | 29.4% | 23.5% | 35.3% |

Figure 7:
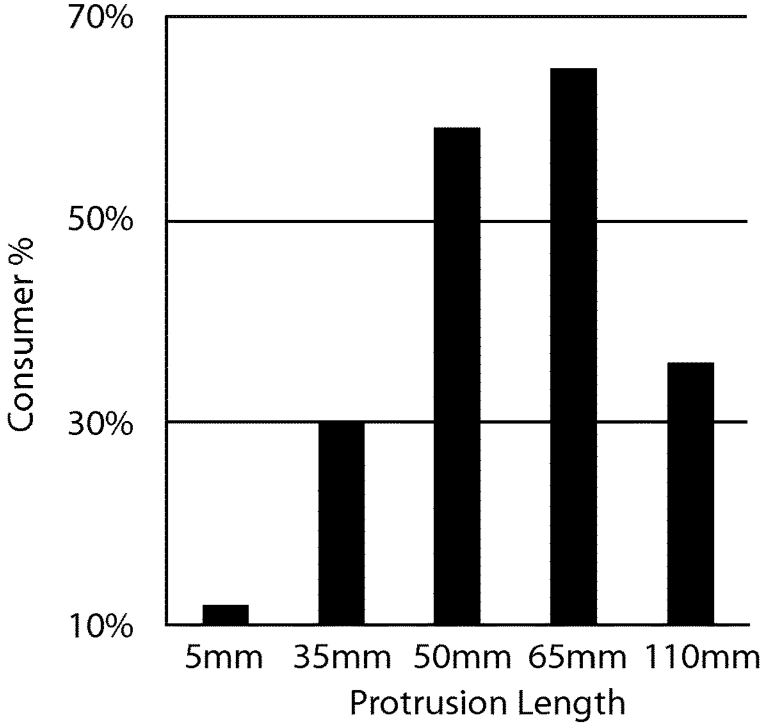
FIG. 7 is a bar graph showing consumer preference for protrusion length.

Referring to Table 1 and FIG. 7, 29.4%, 58.8%, 64.7%, and 35.3% of consumers ranked the 35 mm, 50 mm, 65 mm, and 110 mm lengths as most preferred or second most preferred for precision and control. These numbers were notably higher than the 11.8% of consumers who ranked the 5 mm length as most preferred or second most preferred.

Now referring to Table 2, 17 hair color consumers were asked to simulate using the following extended nozzle foam dispensers with different nozzle angles. The consumers were then asked to rank the nozzle angles based on precision and control for dispensing foam directly onto the hair. A ranking of 1 correlates to the most preferred nozzle angle, and a ranking of 5 correlates to the least preferred nozzle angle. The percentages in Table 2 show how the consumers ranked each nozzle angle, rounded to the nearest tenth. The last column of Table 2 shows the percentage of consumers who ranked each nozzle angle as most preferred or as second most preferred for precision and control.

TABLE 2

| Nozzle Angle | 1 | 2 | 3 | 4 | 5 | 1 + 2 |
|---|---|---|---|---|---|---|
| 70° | 0% | 11.8% | 41.2% | 17.6% | 29.4% | 11.8% |
| 80° | 58.8% | 17.6% | 17.6% | 5.9% | 0% | 76.4% |
| 90° | 23.5% | 58.8% | 11.8% | 5.9% | 0% | 82.3% |
| 100° | 11.8% | 11.8% | 23.5% | 41.2% | 11.8% | 23.6% |
| 120° | 5.9% | 0% | 5.9% | 29.4% | 58.8% | 5.9% |

Figure 8:
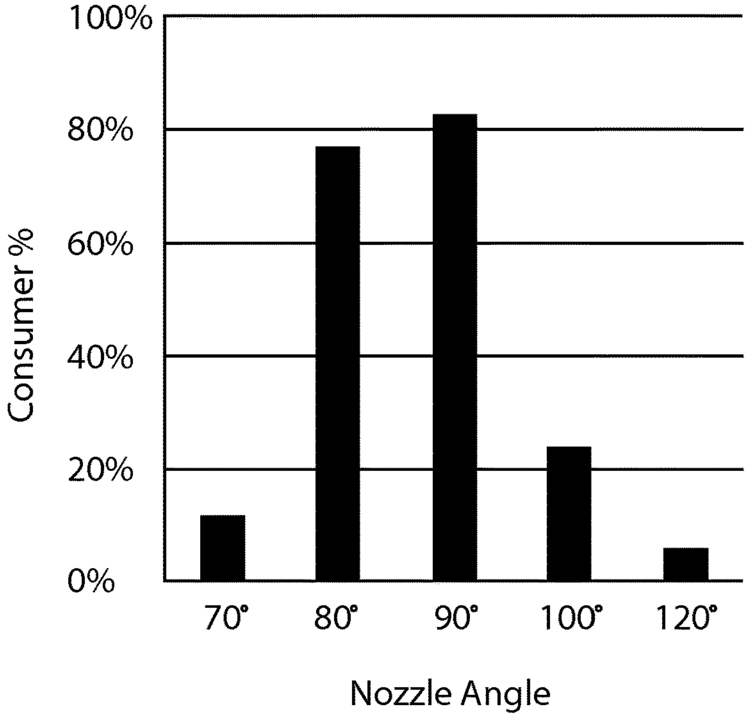
FIG. 8 is a bar graph showing consumer preference for nozzle angle.

Referring to Table 2 and FIG. 8, 76.4% and 82.3% of consumers ranked the 80° and 90° angles as most preferred or second most preferred for precision and control. These numbers were notably higher than the 11.8%, 23.6%, and 5.9% of consumers who ranked the 70°, 100°, and 120° angles as most preferred or second most preferred.

Of the 17 consumers who participated in the above studies, 9 of the consumers stated that they had previously used foam dispensers to color their hair. The 9 consumers who previously used foam dispensers to color their hair were then asked to color their hair using an extended nozzle foam dispenser as described above. When given the opportunity to choose between their old foam dispenser and an embodiment of the present invention, 8 of the 9 consumers (89%) chose an embodiment of the present invention.

In a different study, 10 consumers who previously used liquid dispensers to color their hair were asked to color their hair using an extended nozzle foam dispenser as described above. When given the opportunity to choose between their old liquid dispenser and an embodiment of the present invention, 9 of the 10 consumers (90%) chose an embodiment of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating hair more precisely, the method comprising:

a. providing or obtaining a hair treatment composition in a foam dispenser, wherein the foam dispenser comprises:

i. a reservoir for holding the hair treatment composition;

ii. an extended nozzle directly coupled to the reservoir;

wherein the extended nozzle comprises one or more nozzle orifices disposed therein that are offset from the distal-most end of the extended nozzle;

wherein the one or more nozzle orifices has a total orifice area of from about 5 $mm^2$ to about 80 $mm^2$;

wherein the extended nozzle has a nozzle angle of about 75° to about 85°; and wherein the extended nozzle has a protrusion length of from about 40 mm to about 75 mm;

b. dispensing the hair treatment composition from the reservoir into the extended nozzle and out the one or more nozzle orifices directly onto the hair as a foam by causing the hair treatment composition to travel parallel to an extended nozzle longitudinal axis from a point on the extended nozzle longitudinal axis that intersects with a vertical reservoir axis extending vertically from the outer contour defining the reservoir and until reaching the one or more nozzle orifices; and wherein the foam has a specific volume of from about 6 ml/g to about 10 ml/g;

c. leaving the foam on the hair for from about 5 minutes to about 60 minutes; and d. rinsing the foam from the hair.

2. The method of claim 1, wherein the hair treatment composition has a viscosity of from about 1 cps to about 1,500 cps.

3. The method of claim 1, wherein the foam dispenser is selected from the group consisting of squeeze foam dispensers, aerosol foam dispensers, pump foam dispensers, and combinations thereof.

4. The method of claim 1, wherein the reservoir is composed of a material selected from the group consisting of rigid materials, flexible materials, and combinations thereof.

5. The method of claim 1, wherein the hair treatment composition is either a hair color composition or a hair bleaching composition.

6. The method of claim 1, wherein the total orifice area is from about 12 $mm^2$ to about 50 $mm^2$.

7. The method of claim 1, wherein the foam is dispensed directly onto the hair as a noodle of foam.

8. The method of claim 7, wherein the noodle of foam has an average diameter of from about 5 mm to about 40 mm.

9. The method of claim 1, wherein the extended nozzle further comprises a closed nozzle tip.

10. The method of claim 1, wherein the extended nozzle is selected from the group consisting of detachable nozzles, telescoping nozzles, flexible nozzles, hinged nozzles, and combinations thereof.

11. The method of claim 1, further comprising using the extended nozzle to part the hair.

* * * * *